US00PP13058P2

(12) United States Plant Patent
Brown

(10) Patent No.: US PP13,058 P2
(45) Date of Patent: Oct. 8, 2002

(54) DIASCIA PLANT NAMED 'CODIAW'

(75) Inventor: Graham Brown, Baulkham Hills (AU)

(73) Assignee: Nuflora International Pty. Ltd., Sydney (AU)

( * ) Notice: Subject to any disclaimer, the term of this patent is extended or adjusted under 35 U.S.C. 154(b) by 0 days.

(21) Appl. No.: 09/996,380

(22) Filed: Nov. 30, 2001

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Diascia plant named 'Codiaw', characterized by its upright, outwardly spreading, and compact plant habit; freely and continuous branching; and numerous white-colored flowers with red purple centers.

1 Drawing Sheet

BOTANICAL CLASSIFICATION/CULTIVAR DESIGNATION

*Diascia×hybrida* cultivar Codiaw.

BACKGROUND OF THE INVENTION

The present Invention relates to a new and distinct cultivar of Diascia plant, botanically known as *Diascia×hybrida*, and hereinafter referred to by the cultivar name Codiaw.

The new Diascia is a product of a planned breeding program conducted by the Inventor in Baulkham Hills, New South Wales, Australia. The objective of the breeding program is to create new compact Diascias with numerous uniquely-colored flowers.

The new Diascia originated from a cross made by the Inventor in 1998 of a proprietary selection of *Diascia×hybrida* identified as code number X97.48, not patented, as the female, or seed parent, with a proprietary selection of *Diascia×hybrida* identified as code number X97.52, not patented, as the male, or pollen parent. The new Diascia was selected as a single plant from the resulting progeny by the Inventor in October, 1999, in Cobbitty, New South Wales, Australia, on the basis of its numerous white-colored flowers with red purple centers.

Asexual reproduction of the new cultivar by terminal cuttings taken in Cobbitty, New South Wales, Australia since October, 1999 has shown that the unique features of this new Diascia are stable and reproduced true to type in successive generations.

SUMMARY OF THE INVENTION

Plants of the cultivar Codiaw have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Codiaw'. These characteristics in combination distinguish 'Codiaw' as a new and distinct cultivar:

1. Upright, outwardly spreading and compact plant habit.
2. Freely and continuous branching.

3. Numerous white-colored flowers with red purple centers.

Compared to plants of the female parent, the selection X97.48, plants of the new Diascia are slightly taller and have larger flowers. In addition plants of the new Diascia and the female parent differ in flower color as plants of the selection X97.48 have pink-colored flowers.

Compared to plants of the male parent, the selection X97.52, plants of the new Diascia are slightly taller and have larger flowers. In addition plants of the new Diascia and the male parent differ in flower color as plants of the selection X97.52 have pink-colored flowers.

Plants of the new Diascia can be compared to plants of the Diascia cultivar Ice Cracker, not patented. In side-by-side comparisons conducted in Cobbitty, New South Wales, Australia, plants of the new Diascia were slightly taller and had larger flowers than plants of the cultivar Ice Cracker. In addition, plants of the new Diascia and the cultivar Ice Cracker differed in flower color as plants of the cultivar Ice Cracker were white with a smaller central red purple area.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Diascia.

The photograph at the top of the sheet comprises a side perspective view of three typical flowering plants of 'Codiaw' grown in a 19-cm container.

The photograph at the bottom of the sheet comprises a close-up view of typical leaves, flowering stem, and fully opened flowers of 'Codiaw'.

DETAILED BOTANICAL DESCRIPTION

The aforementioned photographs and following observations and measurements describe plants grown in Encinitas, Calif., in an outdoor nursery under full sunlight conditions during the late winter and early spring with day temperatures averaging 24° C. and night temperatures averaging 12° C. Plants were grown for 16 weeks in 19-cm containers with three plants per container and were pinched one time. Color references are made to The Royal Horticultural Society Colour Chart, version 1995, except where general terms of ordinary dictionary significance are used.

Botanical classification: *Diascia×hybrida* cultivar Codiaw.

Parentage:

*Female parent.*—Proprietary *Diascia×hybrida* selection identified as code number X97.48, not patented.

*Male parent.*—Proprietary *Diascia×hybrida* selection identified as code number X97.52, not patented.

Propagation:

*Type cutting.*—Terminal vegetative cuttings.

*Time to initiate roots, summer and winter.*—About 7 days at 20° C.

*Time to develop roots, summer and winter.*—About 21 days at 20° C.

*Root description.*—Fine and fibrous.

*Rooting habit.*—Freely branching.

Plant description:

*Form/growth habit.*—Upright, outwardly spreading and compact plant habit. Freely branching with more than 30 lateral branches per plant. Moderately vigorous growth habit.

*Plant height.*—About 23 cm.

*Plant diameter.*—Single plant: About 25 cm. Three plants: About 48 cm.

*Lateral branches.*—Aspect: Initially upright, then outwardly arching. Length: About 26 cm. Diameter: About 1.5 mm. Internode length: About 3 cm. Texture: Smooth, glabrous. Color: 144B.

*Foliage description.*—Arrangement: Opposite; simple. Quantity per lateral branch: About 16. Length: About 2.2 cm. Width: About 1.9 cm. Shape: Deltoid to slightly cordate. Apex: Broadly acute. Base: Truncate to cordate. Margin: Slightly serrate. Texture: Smooth, glabrous. Venation pattern: Pinnate. Color: Young and mature foliage, upper surface: 137A. Young and mature foliage, lower surface: 147C. Venation, upper surface: 137B. Venation, lower surface: 147C. Petiole length: About 2 mm. Petiole diameter: About 2 mm. Petiole color: 137C.

Flower description:

*Flower type and habit.*—Solitary axillary flowers; zygomorphic. Five modified petals fused at base: two upper (banner) petals, two lateral petals and one larger lower lip petal. Flowers not persistent. Very freely flowering; typically about 16 buds and flowers per lateral branch. Flowers face mostly outward.

*Natural flowering season.*—Plants typically flower from March through June in the Northern Hemisphere; flowering continuous during this period.

*Flower longevity on the plant.*—About 3 to 4 days.

*Fragrance.*—Not detected.

*Flower size.*—Height: About 2.2 cm. Width: About 2.2 cm. Depth (height): About 8 mm.

*Flower buds (showing color).*—Length: About 4 mm. Diameter: About 6 mm. Shape: Oval. Color: 155A.

*Petals.*—Quantity/arrangement: Five modified petals fused at base: two upper (banner) petals, two lateral petals and one larger lower lip petal. Base of banner petals with indented yellow eyespots; lower surfaces of lateral petals modified into nectar spurs; and lower lip petal convex forming horizontal insect landing platform. Length: Banner petals: About 7 mm. Lateral petals: About 7 mm. Lower lip petal: About 1 cm. Width: Banner petals: About 7 mm. Lateral petals: About 9 mm. Lower lip petal: About 1.4 cm. Lateral petal spur: Length: About 1 cm. Diameter, at petal attachment: About 2 mm. Shape, all petals: Roughly spatulate. Apex, all petals: Rounded. Margin, all petals: Entire. Texture, all petals: Smooth, velvety. Color, all petals: Upper surface, when opening: 155D. Lower surface, when opening: 155C. Upper surface, fully opened: More white than 155C; at base of petals, 59A to 59B; color does not fade with subsequent development. Lower surface, fully opened: More white than 155C. Nectar spurs: 54A. Eyespot on banner petals: 4B.

*Sepals.*—Arrangement/appearance: Single whorl of five sepals fused at base; star-shaped. Length: About 4 mm. Diameter: About 2 mm. Shape: Elliptic. Apex: Acute. Margin: Entire. Texture, upper and lower surfaces: Smooth, glabrous. Color, immature and mature: Upper surface: 144B. Lower surface: 144A.

*Peduncles.*—Length: About 1.2 cm. Width: Less than 1 mm. Angle: About 45° from the stem. Strength: Moderately strong; slender. Texture: Smooth. Color: 144B.

*Reproductive organs.*—Stamens: Quantity per flower: Four. Anther shape: Ovoid. Anther length: Less than 1 mm. Anther color: 14A. Pollen amount: Scarce. Pollen color: 14A. Pistils: Quantity per flower: One. Pistil length: About 4 mm. Style length: About 2 mm. Style color: 144D. Stigma shape: Rounded. Stigma color: 144D. Ovary color: 144C.

*Seed/fruit.*—Seed nor fruit production has not been observed.

Disease/pest resistance: Plants of the new Diascia have not been noted to be resistant to pathogens or pests common to Diascia.

Temperature tolerance: Plants of the new Diascia have been observed to tolerate temperatures from 0 to 32° C.

It is claimed:

1. A new and distinct cultivar of Diascia plant named 'Codiaw', as illustrated and described.

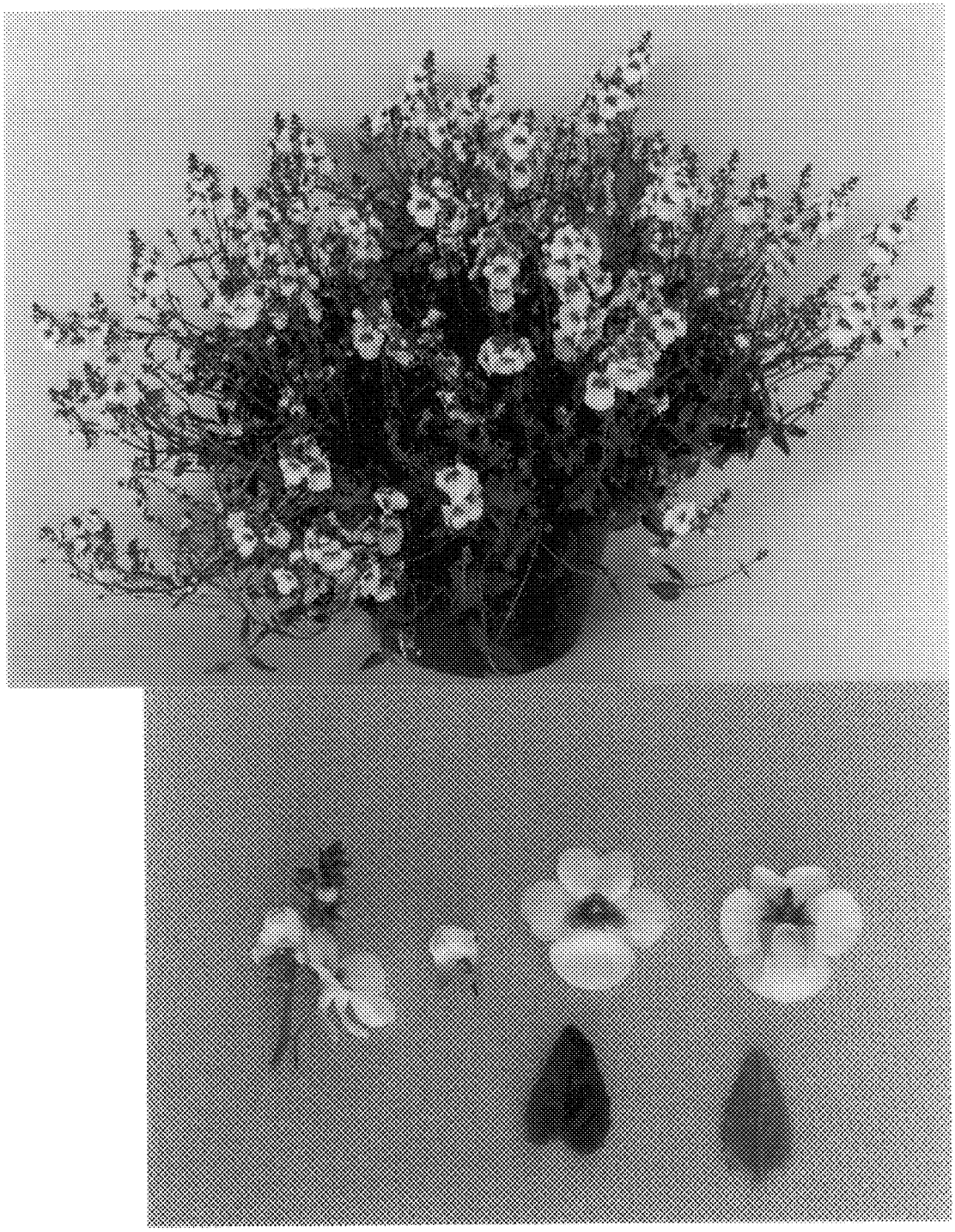

* * * * *